United States Patent [19]

Ashcraft et al.

[11] Patent Number: 5,249,676

[45] Date of Patent: Oct. 5, 1993

[54] FLAVOR BURST STRUCTURE AND METHOD OF MAKING THE SAME

[75] Inventors: Charles R. Ashcraft; Milly M. L. Wong, both of Winston-Salem, N.C.

[73] Assignee: R. J. Reynolds Tobacco Company, Winston-Salem, N.C.

[21] Appl. No.: 35,537

[22] Filed: Mar. 22, 1993

Related U.S. Application Data

[63] Continuation of Ser. No. 696,700, May 7, 1991, abandoned.

[51] Int. Cl.$^5$ .................. A24F 15/08; B65D 85/10
[52] U.S. Cl. ................... 206/264; 206/273; 428/905
[58] Field of Search ............... 206/242, 245, 264, 271; 428/40, 41, 905, 352

[56] References Cited

U.S. PATENT DOCUMENTS

| | | | |
|---|---|---|---|
| 1,589,603 | 6/1926 | Lee | 206/264 |
| 2,046,975 | 7/1936 | Shaw et al. | |
| 2,767,900 | 10/1956 | Bouteloup | 206/264 |
| 2,845,213 | 7/1958 | Tamarin | 206/264 X |
| 3,266,709 | 8/1966 | Whitaker et al. | 206/264 X |
| 3,494,505 | 7/1968 | Huebner et al. | |
| 3,599,859 | 8/1971 | Maierson | 229/238 X |
| 4,145,001 | 3/1979 | Weyenberg et al. | |
| 4,186,743 | 2/1980 | Steiger | |
| 4,254,910 | 3/1981 | Martin | |
| 4,356,115 | 10/1982 | Shibanai et al. | 428/905 X |
| 4,484,768 | 11/1984 | Norfleet | |
| 4,487,801 | 12/1984 | Turnbull et al. | |
| 4,493,869 | 1/1985 | Sweeny et al. | |
| 4,528,226 | 7/1985 | Sweeny | 428/905 X |
| 4,606,956 | 8/1986 | Charbonneau et al. | |
| 4,717,017 | 1/1988 | Sprinkel, Jr. et al. | |
| 4,720,409 | 1/1988 | Spector | 428/905 X |
| 4,720,423 | 1/1988 | Fraser | |
| 4,992,326 | 2/1991 | Dabi | 428/402 X |
| 5,071,704 | 12/1991 | Fischel-Ghodsian | 428/905 X |

Primary Examiner—Steven N. Meyers
Assistant Examiner—Jacob K. Ackun, Jr.
Attorney, Agent, or Firm—Grover M. Myers

[57] ABSTRACT

A flavor burst structure and a method of dispersing a flavorant are disclosed. The flavor burst structure comprises a multilayer film with a flavor carrier layer disposed between barrier layers. The flavor carrier layer comprises a polymeric material blended with a flavorant that is not compatible or is partially incompatible with the polymeric material so that the flavorant desorbs from the carrier layer when one of the barrier layers is removed from the carrier layer. Several package applications are disclosed, including a cigarette package, package tear tapes and the like.

14 Claims, 3 Drawing Sheets

FLAVOR BURST STRUCTURE AND METHOD OF MAKING THE SAME

This is a continuation of co-pending application Ser. No. 07/696,700 filed on May 7, 1991 and now abandoned.

FIELD OF THE INVENTION

The present invention relates to a flavor burst structure article, and a method of making the same. More particularly, the invention relates to a multilayer flavor burst film article, a package incorporating the article and a method of making the package in which a flavor or fragrance is preserved in the package and released as a burst of the flavor or fragrance when the package is opened so as to provide an immediate olfactory sensation to the consumer and to others in the near vicinity.

DESCRIPTION OF THE PRIOR ART

It is well known to blend a flavorant with a polymeric material. It is also known to incorporate a flavor, fragrance or an aromatic substance in a package, such as a cigarette package, in such a way that the flavor, fragrance or aromatic substance is released when the package is first opened. "Flavor," "fragrance," "aromatic substance" and like terms are used interchangeably herein and are intended to include any substance that is capable of causing an olfactory sensation, including substances such as flavorants, perfumes, odorants, deodorants and scents.

One known flavor-releasing package is disclosed in U.S. Pat. No. 4,717,017 which describes a cigarette pack in which the package overwrap film is provided with a sealed receptacle containing a volatile fragrance or flavor which overlies the tear tape of the cigarette pack. When the tear tape is pulled to slit the overwrap and open the pack, it also ruptures the receptacle and releases the fragrance or flavor contained in the receptacle to convey a desired impression, such as freshness.

U.S. Pat. No. 4,145,001 discloses another form of package for the controlled release of a volatile deodorizer, such as a room air freshener, in which an absorbent pad carrying the volatile deodorizer is sandwiched between two laminated multilayer sheets with outer impermeable layers. The package is opened by delaminating one of the sheets at the interface between two selected layers so that the volatile deodorizer is covered on one side only by a permeable layer which allows controlled release of the volatile deodorizer over a period of time.

U.S. Pat. No. 4,254,910 discloses another packaging system for the controlled release of volatile substances, such as air fresheners, in which a volatile material is sealed on both sides of a two-layer, separable permeable sheet by a pair of impermeable sheets heat sealed on opposite sides of the permeable sheet to form a package with an outer impermeable layer. When the package is separated at the two-layer permeable sheet, the volatile substance is released through each of the exposed permeable sheets.

U.S. Pat. No. 4,720,423 describes a package for consumables which includes an overwrap with a tear strip for slitting the overwrap and opening the package. The tear strip comprises two layers of material bonded together by an adhesive which contains fragrance-bearing microcapsules. When the outer layer of the tear strip is pulled to open the package, the microcapsules are ruptured and release the fragrance contained therein.

SUMMARY OF THE INVENTION

The present invention is directed to a flavor burst structure comprising a coextruded or laminated multilayer polymeric film. The flavor burst film may comprise an inner or flavor carrier layer in which a polymeric material and a flavorant have been compounded or blended together and an outer polymeric barrier layer on each side of the flavor carrier layer to retain and preserve the flavorant in that layer until one or both of the outer barrier layers is removed from the flavor carrier layer to expose the surface or surfaces of the flavor carrier layer and thereby release the flavorant.

The flavor burst film may also comprise the aforesaid flavor carrier layer, a first polymeric barrier layer on one side of the flavor carrier layer and a second barrier layer on the other side of the flavor carrier layer, wherein the second barrier layer may be a flexible foil or rigid substrate made of a material such as metal, glass or any other suitable barrier material. The flavorant may be released from the carrier layer when the first barrier layer is removed from the flavor carrier layer, when the flavor carrier layer and the first barrier layer are removed from the second barrier layer, or when the flavor carrier layer is removed from both barrier layers.

The preferred form of the flavor burst structure of the invention is a film in which one of the two outer barrier layers is bonded to the flavor carrier layer with an adhesive layer that provides a stronger bond between such barrier layer and the flavor carrier layer. In that form, a force applied to one or both of the outer barrier layers of the film which tends to delaminate or separate the layers will cause separation of the film at a selected interface between the film layers, namely, at the interface between the barrier layer and the flavor carrier layer that has no adhesive layer. This preferred form of the flavor burst film is especially suited for use in packages where it is intended that the flavor carrier layer remain with the package for releasing a burst of flavor when the package is opened and for a period of time after the package is opened.

Alternatively, the layers may be formulated to have different adhesion strengths between the flavor carrier layer and each of the outer barrier layers so as to achieve separation at a selected interface between the layers.

Examples of polymer materials that may be used as the flavor carrier layer include, but are not limited to, high density polyethylene (HDPE), low density polyethylene (LDPE), polypropylene, polyvinylacetate, polyethylenevinylalcohol, polyethyleneterephthalate-glycol copolymer, polyethyleneterephthalate, polyvinylalcohol, polyamides, such as nylon, nylon/acrylate copolymers, polyacrylonitrile/styrene copolymer, Surlyn ® (ionomer), polystyrene, and blends of the above materials. Virtually any polymeric resin that can be made into a film can be used as the flavor carrier layer.

Examples of polymer materials that may be used as the barrier layers include, but are not limited to, polyethylenevinylalcohol (EVOH), polyvinyl alcohol and its copolymers, polyamides, polyacrylonitrite and its copolymers, polyethyleneterephthalate and its copolymers and polyvinylidenechloride and its copolymers. It would also be possible to use a polymer layer having a metallized coating applied to one side thereof by vacuum deposition or other conventional metallizing process or by lamination of a metal foil to the polymer layer. One of the barrier layers may also comprise a metal or glass layer, such as a metal or glass food or beverage container.

Flavors that may be compounded or blended with the polymeric material of the carrier layer include, but are not limited to, aromatic/aliphatic ketones (e.g. Carvone), aromatic/aliphatic aldehydes (e.g. p-Tolualdehyde), aromatic/aliphatic alcohols, phenols and esters (e.g. Menthol and Methyl salicylate), gamma and delta-lactones (e.g. gamma-Nonalactone), aliphatic/aromatic acids (e.g. Phenylacetic acid), aromatic/aliphatic oxides/ethers (e.g. 1,8-Cineole), and heterocyclic analogs of the above. In addition to the foregoing aromatic chemicals, other types of flavors, such as essential oils, absolutes, plant extracts, oleoresins, tinctures, botanical flavoring materials, reaction flavors, and flavors derived from plants, e.g. tobacco, may be used. Certain flavorants may provide the impression of a gustatory (taste) sensation as well as an olfactory sensation. Such flavorants are useful in enhancing the consumer's perception of a product, especially food products. It is also within the scope of the invention to provide a substance that has an unpleasant odor for blending with the polymer of the carrier layer. A flavor burst film using such a carrier layer could be used, for example, to provide an olfactory warning much the same as hydrogen sulfide might be used to odorize an otherwise odorless gas. Such a warning may be used to make packages for chemicals and cleaners child resistant.

It has been found unnecessary to encapsulate or completely surround the flavor carrier layer with the barrier layer material in order to preserve the flavor in the carrier layer for a substantial period of time, e.g., the expected shelf life of the product in which the flavor burst film is packaged. Flavor loss studies have shown surprisingly that the amount of flavor loss from the edges of the flavor carrier is essentially insignificant. It is believed that this phenomenon is the result of an equilibrium gradient at the edges of the flavor carrier layer whereby a very slight loss of flavor from the polymeric material at the edges of the carrier layer forms an effective barrier to the passage of the flavorant from the greater mass of the carrier layer located inwardly of the edges.

The invention is also directed to a package in which the above-described flavor burst film has been incorporated. In one embodiment of a package with a heat sealable overwrap, such as a cigarette package, a section of flavor burst film of the above-described preferred form is adhesively bonded to the pack closure or tax stamp or to the top surface of the package with the releasable or separable barrier layer located outwardly. A heat sealable layer is applied to or coextruded over the outer surface of the separable barrier layer so that when the overwrap is heat sealed at the top of the package it will be heat sealed to the outer barrier layer of the flavor burst film. When the cigarette package is opened by a conventional tear tape, the heat sealed portion of the overwrap at the top of the package will be pulled away along with the heat sealed outer barrier layer which separates from and exposes the entire outer surface of the flavor carrier layer. The flavorant is simultaneously released from the carrier layer to provide a burst of flavor that is immediately perceptible to anyone in the near vicinity of the package.

Preferably, the flavor persists for a period of time commensurate with the product involved. In the case of a package of cigarettes in which the flavor burst film releases a menthol or vanillin flavor, for example, a persistence of 24-48 hours is desirable. In an air freshener application, release of the flavor is desired over a relatively long period of time, such as a few weeks. Such long term release may be accomplished by gradually exposing the surface of the flavor carrier layer, e.g., by periodically peeling away successive portions of the barrier layer to expose corresponding portions of the underlying carrier layer.

In an alternative embodiment of the package of the invention, also for use with an overwrapped package with a tear tape, a strip of the flavor burst film is adhesively bonded to the package beneath the overwrap so that the entire tear tape or a portion thereof overlies the flavor burst film and is adhesively bonded to the separable barrier layer of the film. To open the package the tear tape is pulled to slit the overwrap. At the same time, the tear tape separates the outermost barrier layer from the flavor burst film thereby exposing the surface of the flavor carrier layer and simultaneously releasing a burst of flavor from the film.

In another alternative embodiment of the invention, the flavor burst film is incorporated in the tear tape of an overwrapped package. The tear tape is formed as a multilayer coextruded film comprising a 2-3 mil thick layer of oriented polypropylene (OPP) a first adhesive layer, a first barrier layer, a flavor carrier layer, a second adhesive layer and a second barrier layer. The OPP layer functions structurally as the tear tape and is attached to the overwrap with a suitable material such as a conventional wax coating. The second barrier layer is coated or coextruded with an adhesive layer which is adhered to the package so that the multilayer tear tape film is interposed between the overwrap and the underlying package wrapper. The tear tape is scored or transversely slit through the second barrier layer, second adhesive layer and flavor carrier layer so that when the tear tape is grasped at its free end and pulled, the first barrier layer, first adhesive layer and OPP layer separate from the underlying flavor carrier layer exposing the carrier layer surface and thus releasing the flavor.

Although the embodiments of the present invention have been described in connection with overwrapped packages having a tear tape, and particularly cigarette packages, it will be appreciated by those skilled in the art in light of the teachings herein that the present invention has a variety of applications other than packaging tobacco products, including (1) the packaging of many comestibles that may or may not utilize an overwrap with a tear tape, such as dairy products (ice cream, cheese spreads, etc.), beverages (wines, soft drinks, etc.), cereals, cake mixes, snacks, baked goods, confections and the like, and (2) the packaging of other consumer products, such as pharmaceuticals, paper products, and cleaning products. In such packaging applications, the flavor barrier film of the invention may be incorporated into the overlapping flaps of the package closure such that, when the flaps are separated to open the package, the flavor burst film is also separated. A package inner wrap may also incorporate a flavor burst film that would be separated when the inner wrap is opened, i.e., by peeling, tearing, etc. The flavor burst film may be adhered between the inner wrap seal by heat seal layers or adhesive layers. A flavor burst film comprising one barrier layer and a flavor carrier layer may be applied to the surface of a metal or glass container or package so that removal of the one barrier layer will release the flavorant.

In addition to packaging applications, the present invention is useful in those industries that directly involve fragrances, such as perfumery, cosmetics, health care, air fresheners, and toiletries. For instance, fragrance samples for perfumes, cosmetics, toiletries and the like may be prepared as flavor burst films according to the present invention.

According to the method of the present invention, a flavorant is blended with a polymeric material which is not compatible or is partially incompatible with the flavorant. The terms "not compatible" and "partially incompatible" as used herein mean the ability of the polymeric material to exclude the flavorant from the interstices of the polymeric matrix. In other words, the polymeric material does not hold the flavor well. The flavor-carrying polymer may be coextruded between two polymer layers which provide a barrier to the release of the flavorant from the opposite sides of the flavor carrier. An adhesive layer may be coextruded between the flavor carrier layer and one of the barrier layers to provide a multilayer film which is selectively separable between the flavor carrier layer and the other one of the barrier layers. Separation of one of the barrier layers releases a burst of flavor from the flavor carrier layer.

Advantageously, the present invention provides for releasing a flavor burst by desorption of the flavorant from a polymeric material in which the flavorant has been compounded. Thus, the flavorant is released as a volatile substance directly from the amorphous regions or interstices of the polymeric material matrix and requires neither microencapsulation of the flavorant nor any other form of rupturable receptacle to contain the flavorant substance. In addition, because the flavor carrier layer of the flavor burst film is disposed between two barrier layers, the flavorant will not be absorbed by the contents of the package to which the flavor burst film is applied.

With the foregoing and other advantages and features of the invention that will become hereinafter apparent, the nature of the invention may be more clearly understood by reference to the following detailed description of the invention, the appended claims and to the several views illustrated in the attached drawings.

DETAILED DESCRIPTION OF EMBODIMENTS OF THE INVENTION

Figure 1:
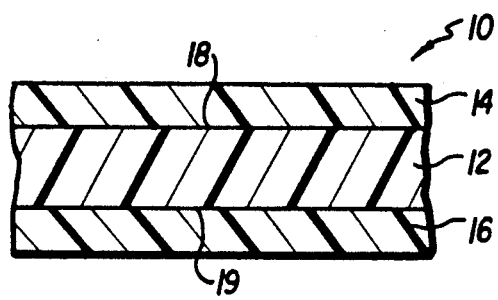
FIG. 1 is a cross-sectional view of one embodiment of a flavor burst film according to the present invention.

Referring now in detail to the drawings, there is illustrated in FIG. 1, greatly enlarged, a first embodiment of a flavor burst structure according to the invention which is designated generally by reference numeral 10. Flavor burst structure 10 is a film comprising a flavor carrier 12, preferably a 1-2 mil thick layer of a high density polyethylene (HDPE) material in which a flavorant, such as menthol, vanillin, etc., or combination of flavorants, has been blended in amounts of from 1 to 20% by weight. Barrier layers 14, 16 are disposed on opposite sides of the flavor carrier layer 12 and comprise a polyethylenevinylalcohol (EVOH) material. The layers 12-16 of film 10 may be laminated but are preferably coextruded.

Barrier layers 14, 16 serve to retain the flavorant in the carrier layer 12 for a period of time commensurate with the desired shelf life of the film. Shelf life can be controlled by appropriate selection of the composition of the materials of the carrier and barrier layers, their thicknesses, the amount and type of flavorant compounded in the carrier layer, and the compatibility of the flavorant with the carrier layer, etc. In light of the teachings herein, one of ordinary skill in the art would be capable of making an appropriate selection of the foregoing parameters of the film layers to achieve a desired shelf life. One of the barrier layers 14, 16 may be a metal or glass layer, such as a metal or glass container to which a two layer flavor burst film, i.e., a flavor carrier layer and one barrier layer, is applied.

To release the flavorant contained in the carrier layer 12, i.e., to activate the flavor burst film 10, one or both of the barrier layers 14, 16 are removed or peeled from the carrier layer 12 exposing surface 18 and/or surface 19 of the carrier layer. Immediately upon exposure of surface 18 and/or 19, the flavorant compounded in carrier layer 12 begins to desorb from layer 12 and is released as a volatile into the air surrounding the film 10. Thus, a person in the near vicinity of the activated film 10 experiences an immediate olfactory sensation. Depending on the particular type of flavorant or combination of flavorants used in the film, the olfactory sensation created may provide the person with a perception of freshness, cleanliness or other favorable attribute or it may suggest a particular product, e.g., tobacco and menthol flavors to suggest a menthol cigarette. The impression of a gustatory sensation may also be elicited with familiar volatile flavorants.

Figure 2:
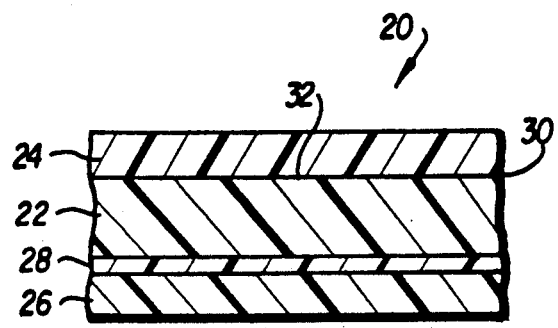
FIG. 2 is a cross-sectional view of a preferred embodiment of a flavor burst film according to the invention.

FIG. 2 illustrates a preferred embodiment of the flavor burst film of the invention designated generally by reference numeral 20. Film 20 comprises the same layers as the FIG. 1 embodiment, namely, a flavor carrier layer 22, and two barrier layers 24, 26 disposed on opposite sides of the carrier layer 22. Interposed between carrier layer 22 and barrier layer 26 is an adhesive layer 28 about 0.05 to 0.1 mils thick, which may be a maleic anhydride modified polyolefin adhesive layer or any other suitable adhesive that will provide a stronger bond between carrier layer 22 and barrier layer 26 than exists between carrier layer 22 and barrier layer 24.

In the FIG. 2 embodiment, outwardly directed forces applied to the barrier layers 24, 26 will cause the film 20 to separate or delaminate along a selected interface, namely, the interface 30 between barrier layer 24 and carrier layer 22. Such separation will expose surface 32 of the flavor carrier layer 22 and release the flavorant from the carrier layer as described above in connection with FIG. 1. This form of the invention is particularly suited for applications in which the flavor burst film 20 is attached to an object or package from which it is desired to release a burst of flavor, for example, when the package is opened and during use of the product contained in the package. Exemplary embodiments of several such applications are shown in FIGS. 3-9.

Figure 3:
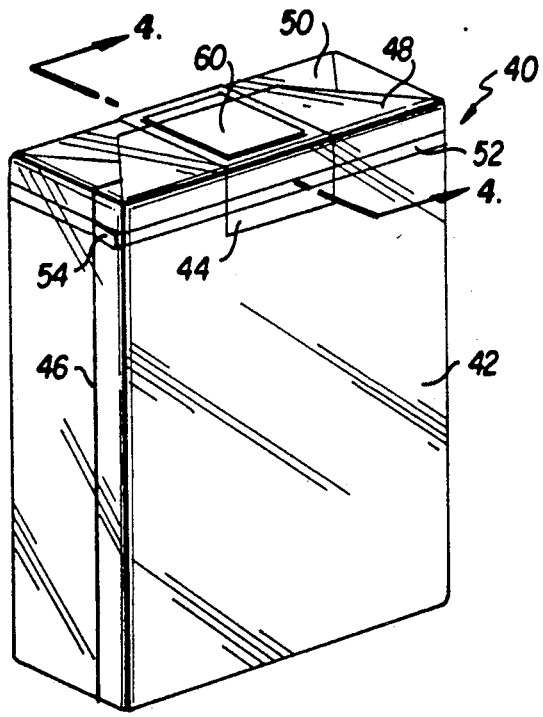
FIG. 3 illustrates in perspective view a cigarette package incorporating one embodiment of the flavor burst film of the invention.
Figure 4:
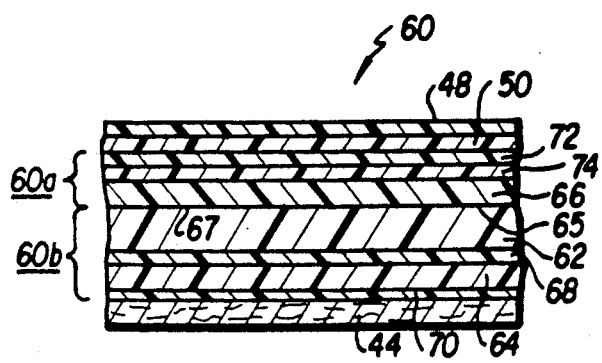
FIG. 4 is a cross-sectional view taken along line 4—4 in FIG. 3 illustrating the manner in which the flavor burst film is adhered to the cigarette package components.
Figure 5:
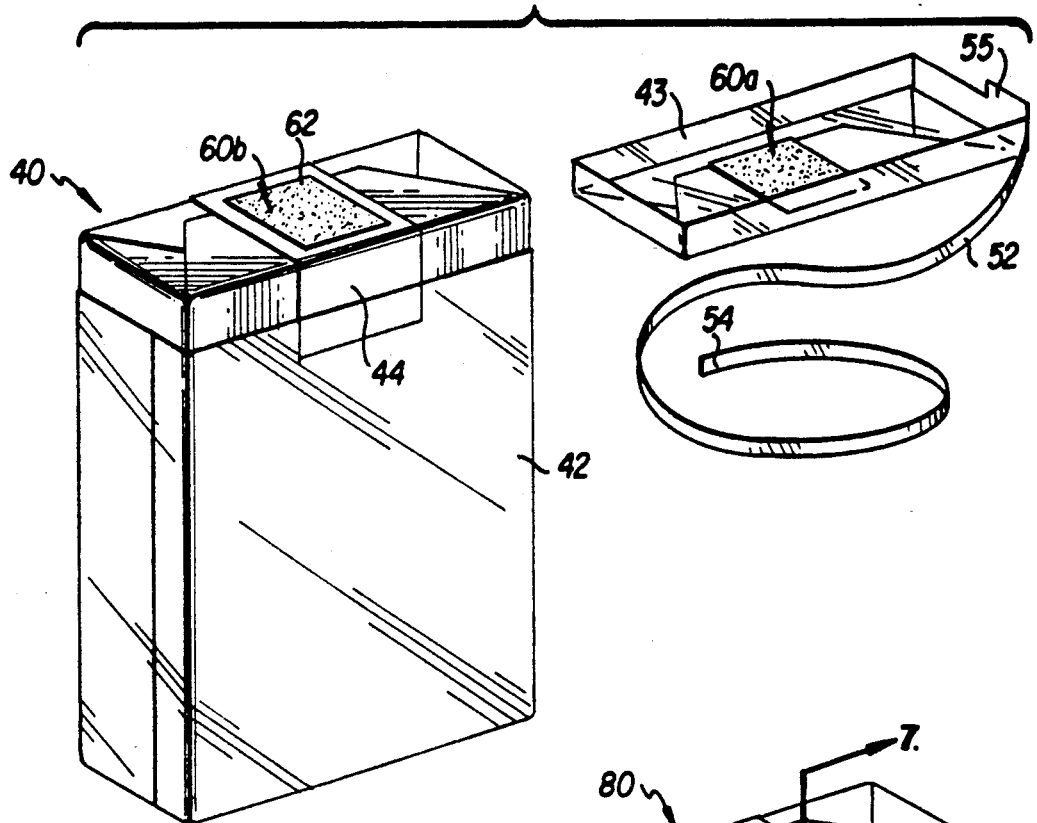
FIG. 5 is a perspective view of the cigarette package of FIG. 4 illustrating the manner in which the flavor is released from the package.

Referring now to FIGS. 3-5, there is illustrated a cigarette package 40 of generally rectangular parallelepiped form. Conventional cigarette packages are one of two types, a so-called "soft pack" as shown in FIGS. 3-5 and a so-called "hard pack," "crush-proof box," or "hinged lid package." Such conventional cigarette packages typically comprise three separate wrappings: (1) an inner foil liner comprising a metal foil laminated to a paper substrate or a metallized paper which is wrapped about the cigarettes and folded at the ends of the cigarettes; (2) a "soft" or "hard" paper or paperboard package or label which is usually imprinted with brand specific information; and (3) an exterior clear overwrap of a heat sealable polymeric film which is heat sealed.

A strip of polymeric material known as a "tear tape" is provided for easy opening of the polymeric overwrap films. The tear tape is positioned adjacent and parallel to the top edge of the package. One end of the tear tape projects slightly from the package as a tab. To open the package, the tab is pulled by the smoker to remove the top of the polymeric overwrap. In particular, the projecting tab of the tear tape is pulled to slit the polymeric overwrap along both edges of the tear tape and the polymeric overwrap covering the top of the container is removed. The top of the package is then opened, i.e., the foil inner liner is torn open in the case of the soft pack or the hinged lid of the hard pack is pivoted open and a portion of the foil inner liner is removed to expose the ends of the cigarettes contained therein. The smoker then grasps the end, usually the filter end, of a cigarette with his/her fingers to remove it from the package. The present invention is suitable for use with both the "soft pack" and the "hard pack" types of cigarette packages.

The cigarette package 40 is shown in FIG. 3 with a transparent overwrap 42 of a heat sealable polymeric film, such as oriented polypropylene (OPP), which is wrapped about an inner foil liner and a paper label (not shown in FIG. 3). The inner foil liner is folded over at the top and bottom of the package and is closed at the top by a pack closure 44 which may also comprise a revenue or tax stamp. The transparent overwrap 42 is wrapped about the cigarette package and is heat sealed adjacent a longitudinal seam 46, then folded over the package at the top and bottom with trapezoidally-shaped flaps 48, 50 and heat sealed. A tear tape 52 with a projecting end tab 54 is provided for slitting the overwrap adjacent the top edge of the package 40. A flavor burst film 60 made according to the invention and having a substantially square shape is affixed to the pack closure 44 and the top flaps 48, 50 as described hereinafter in connection with FIG. 4.

FIG. 4 illustrates in fragmentary, greatly enlarged cross-section the manner in which the flavor burst film 60 is affixed to the cigarette package 40 of FIG. 3. Film 60 comprises a flavor carrier layer 62, two barrier layers 64, 66 and an adhesive layer 68 disposed between carrier layer 62 and barrier layer 64. The layers 62, 64, 66, 68 thus correspond to the preferred form of the flavor burst film shown in FIG. 2 so that the carrier layer 62 and barrier layer 66 are separable at interface 65 to expose the top surface 67 of carrier layer 62. In this embodiment, the film 60 further comprises an adhesive layer 70 for adhesively bonding the film 60 to the paper pack closure 44. Adhesive layer 70 is preferably a pressure sensitive adhesive. A heat seal layer 72 is adhesively bonded to the uppermost barrier layer 66 by an adhesive layer 74, such as Tycel 7283, a urethane type adhesive available from Lord Chemicals. Heat sealed layer 72 is sealed to the flaps 48, 50 of the polymeric overwrap film 42 when the flaps 48, 50 are folded over and heat sealed during manufacture of the cigarette package 40.

It will be understood from the foregoing that the flavor burst film 60 of this embodiment may comprise a coextrusion of the seven layers 62, 64, 66, 68, 70, 72, 74 or a coextrusion of the four layers 62, 64, 66, 68 to which layers 70, 72, 74 are subsequently added by well known coextrusion or coating techniques. Preferably, the seven layer coextruded flavor burst film 60 is applied to the pack closure 44 for use in conventional cigarette packaging machinery and is therefore applied to the cigarette package with the pack closure just prior to the point at which the package is overwrapped with film 42.

FIG. 5 illustrates the manner in which the flavor burst film 60 is activated upon opening the cigarette package 40. When a consumer wishes to open the package 40, he grasps the tab 54 at one end of tear tape 52 and pulls it to slit the overwrap film 42 adjacent the upper edge of the package. The other end 55 of the tear tape 52 is affixed to the heat sealed top portion 43 of the overwrap so that when the overwrap portion 43 is separated from the package it carries with it the film portion 60a comprising heat seal layer 72, adhesive layer 74 and the topmost barrier layer 66. The film portion 60b comprising adhesive layer 70, barrier layer 64, adhesive layer 68 and flavor carrier layer 62 remain affixed to the pack closure 44 with the flavor carrier layer 62 exposed for release of the flavorant as described above.

It is, of course, possible to locate the flavor burst film 60 at another location on the top of the package 40, for example, on the folded flaps of the inner foil wrap to one side or the other of the pack closure.

Figure 6:
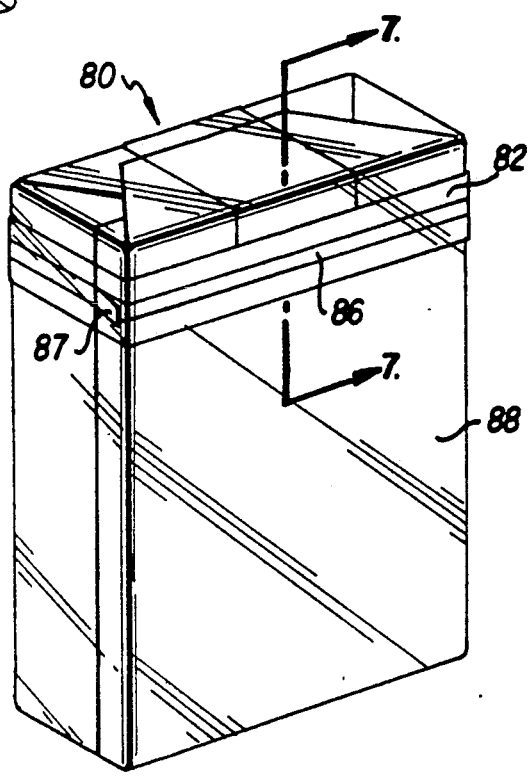
FIG. 6 is a perspective view of a cigarette package incorporating an alternate embodiment of the flavor burst film of the invention.
Figure 7:
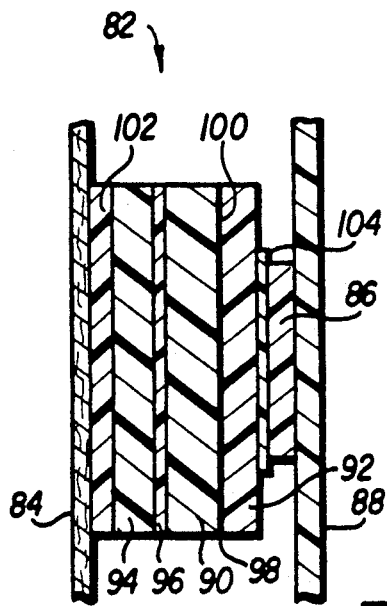
FIG. 7 is a cross-sectional view taken along line 7—7 in FIG. 6 illustrating the manner in which the flavor burst film is adhered to the cigarette package components.

FIGS. 6 and 7 illustrate an alternate embodiment of the invention also for use with a cigarette package 80. In this embodiment, an elongated flavor burst film 82 is adhesively affixed to the paper label 84 (FIG. 7) around the perimeter of the cigarette package in a position to underlie the tear tape 86 and the polymeric overwrap film 88. The flavor burst film 82 comprises a flavor carrier layer 90, two barrier layers 92, 94 and an adhesive layer 96 between barrier layer 94 and flavor carrier layer 90. As before, the layers 90, 92, 94, 96 comprise the preferred form of the flavor burst film described above in connection with FIG. 2 with barrier layer 92 separable at interface 98 to expose surface 100 of the carrier layer 90 and release the flavorant.

An adhesive layer 102 is provided on the other side of barrier layer 94 for bonding the flavor burst film 82 to the paper label 84 of the cigarette package. Another adhesive layer 104 is provided between barrier layer 92 and tear tape 86 to affix barrier layer 92 to the tear tape 86 which is, in turn, affixed to the overwrap 88 in a conventional manner. If desired, adhesive layer 104 may cover the entire surface area of barrier layer 92 so that the overwrap film 88 may also bond to the barrier layer 92 on both sides of the tear tape 86.

Preferably, the flavor burst film 82 comprises coextruded or laminated layers 90, 92, 94 and 96. Adhesive layers 102 and 104 are applied to the label 84 and tear tape 86 during manufacture of the cigarette package. The flavor burst film 82 is activated by grasping the end tab 87 of the tear tape 86 and pulling the tear tape away from the package to slit the overwrap 88. Because the tear tape 86, and optionally, the slit portion of the overwrap film, is adhesively bonded to the separable barrier layer 92, such layer separates from the flavor burst layer 90 and exposes the surface 100 thereof to release the flavorant contained in layer 90.

Figure 8:
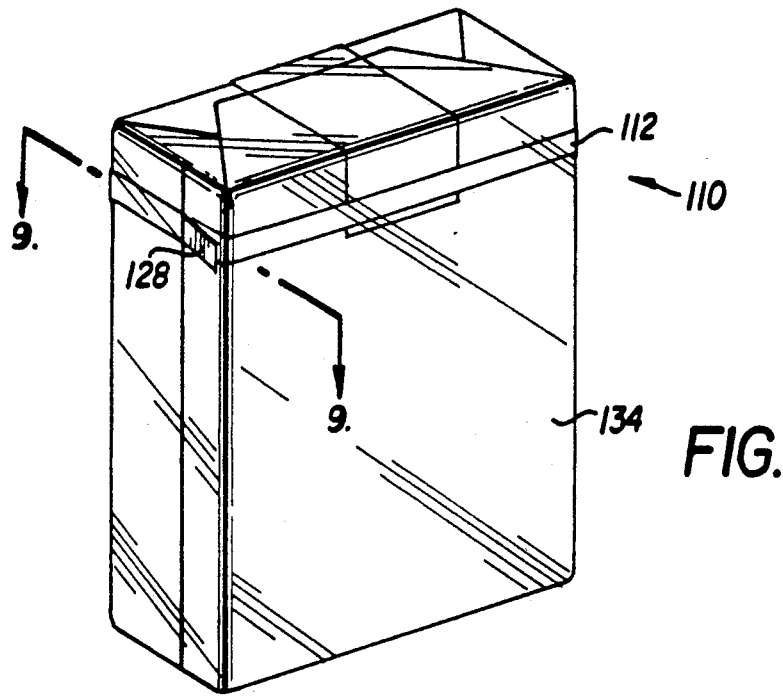
FIG. 8 is a perspective view of a cigarette package incorporating another embodiment of the flavor burst film of the invention in the tear tape of the package.
Figure 9:
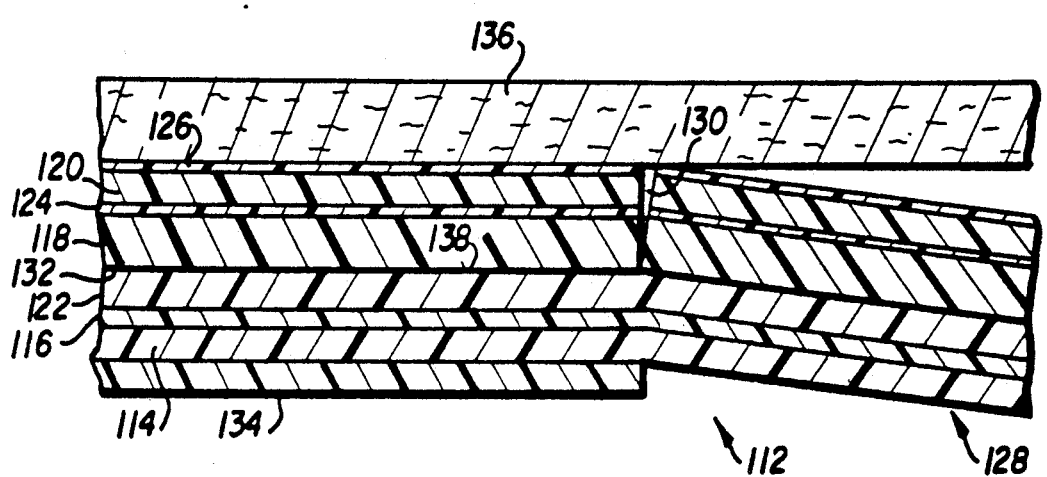
FIG. 9 is a cross-sectional view taken along line 9—9 in FIG. 8 illustrating the manner in which the flavor burst film is incorporated in the tear tape.

Another alternate embodiment of the invention is illustrated in FIGS. 8 and 9. This embodiment of a cigarette package 110 is activated in the same manner as the embodiment of FIGS. 6 and 7, the difference being that the flavor burst film of this embodiment is incorporated as part of the tear tape itself. As best seen in FIG. 9, a multilayer tear tape 112 having seven layers comprises a polymeric substrate film 114, such as the usual tear tape film, an adhesive layer 116, a flavor carrier layer 118, two barrier layers 120, 122, adhesive layer 124 between barrier layer 120 and carrier layer 118 and another adhesive layer 126.

The tear tape 112 is provided with an end tab 128 which is formed by slitting through the layers 118, 120, 124, 126 of the tape 112 as shown at 130 to the interface 132 between barrier layer 122 and flavor carrier layer 118. The tear tape 112 is assembled to the cigarette package overwrap 134 in the conventional manner so that when the overwrap 134 is wrapped about the package, the adhesive layer 126 is affixed to the label 136.

To activate this embodiment, the end tab 128 is grasped and pulled so that the tear tape separates or delaminates along interface 132 thereby exposing the surface 138 of the flavor carrier layer and releasing the flavorant therefrom. It would also be possible to make barrier layer 122 of a material sufficiently strong to function as a tear tape so that the conventional tear tape film 114 and adhesive layer 116 could be eliminated.

EXAMPLES

Flavor burst films were prepared according to the following procedure:

EXAMPLE 1

The base flavor burst film was produced using a five layer coextrusion blown film line. The film consisted of four layers as follows: layer 1–0.5 mil of polyethylenevinylalcohol, layer 2–0.1 mil of a maleic anhydride modified polyethylene, layer 3–2.0 mil of a 5/95 blend by weight of menthol/high density polyethylene, layer 4–0.5 mil of polyethylenevinylalcohol. Layers 1 and 4 are 38% ethylene polyethylenevinylalcohol, such as EVAL EPE made by EVAL Company of America, Lisle, Ill. Layer 2 is Admer QF500 made by Mitsui Petrochemicals (America), Ltd. of New York, N.Y. Layer 3 is HDPE 6187 made by Quantum Chemical, New York, N.Y. blended with 5% menthol by weight. A conventional cigarette overwrap material available from Mobil Chemical Films Division, Macedon, N.Y., was adhesively laminated to layer 4 using a solventless urethane adhesive. A high vinylacetate pressure sensitive adhesive was applied to layer 1.

The flavor burst film with adhesives on both sides was then cut into one inch squares. A square was applied to a cigarette package closure with the pressure sensitive adhesive. The package was then wrapped with an OPP overwrap which was heat sealed to the terpolymer layer.

The packs were stored at room temperature for six months. No menthol odor was apparent before the packs were opened. Upon opening the packs and separation of the flavor burst film, a strong burst of menthol was noted.

EXAMPLE 2

The base flavor burst film was produced on a three layer coextrusion blown film line. The film consisted of three layers as follows: layer 1–0.5 mil of polyethylenevinylalcohol, layer 2–1.5 mil of 10/90 blend of menthol/ionomer, layer 3–0.5 mil of polyethylenevinylalcohol. High vinylacetate pressure sensitive adhesives were added to layers 1 and 3.

The flavor burst film was then slit to 0.2 inches wide and applied to a layer of tear tape. The flavor burst composite structure was then affixed to the overwrap of a cigarette package in a conventional manner such that the flavor burst film was adhered both to the inner and outer wrapper by means of the previously mentioned pressure sensitive adhesives.

The packs were stored at room temperature for six months. No menthol odor was apparent before the packs were opened. Upon opening the packs and separation of the flavor burst film, a strong burst of menthol was noted.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A flavor releasing article comprising a cigarette package containing a plurality of cigarettes, said package having an inner wrap and an overwrap, a flavor burst film disposed between said inner wrap and said overwrap, said inner wrap having a top, said flavor burst film comprising a flavor carrier layer having opposite surfaces and being composed of a polymeric material having a polymeric matrix, a flavorant blended with said polymeric material such that said flavorant is contained in the polymeric matrix and is capable of being released from the opposite surfaces of the flavor carrier layer, first and second barrier layers disposed on a respective one of the opposite surfaces of the flavor carrier layer for retaining the flavorant in the flavor carrier layer, said first barrier layer being affixed to the top of said inner wrap and said second barrier layer being affixed to a portion of said overwrap overlying the top of asid inner wrap, a tear tape formed independently of and separate from said flavor burst film for detaching said overwrap portion from the top of the inner wrap, said second barrier layer being separable from the flavor carrier layer such that when said overwrap portion is detached from the top of the inner wrap by said tear tape, said second barrier layer, said overwrap portion and said tear tape separate from the flavor carrier layer and said first barrier layer and said flavor carrier layer remain attached to the top of the inner wrap whereby only one of the surfaces of the flavor carrier layer is exposed and the flavorant is released therefrom.

2. The article of claim 1, including an adhesive layer between said first barrier layer and said flavor carrier layer for preventing separation therebetween.

3. The article of claim 1, wherein the top of the inner wrap includes flaps and a pack closure disposed over said flaps, said first barrier layer being affixed to said pack closure.

4. The article of claim 1, wherein said flavor carrier layer is high density polyethylene.

5. The article of claim 1, wherein said barrier layers are composed of a polymeric material which forms a substantial barrier to the passage of the flavorant therethrough.

6. The article of claim 1, wherein said flavor carrier layer is high density polyethylene and said barrier layers are polyethylenevinylalcohol.

7. The article of claim 1, wherein said flavorant is menthol.

8. The article of claim 1, wherein said flavor burst film is coextruded.

9. The article of claim 1, wherein aid flavor burst film is laminated.

10. The article of claim 1, wherein said flavor burst film comprises from one side to the other, a first adhesive layer, said first barrier layer, a second adhesive layer, asid flavor carrier layer, said second barrier layer and a heat seal layer.

11. The article of claim 1, including a first heat seal layer affixing said first barrier layer to the top of said inner wrap and a second heat seal layer affixing asid second barrier layer to said overwrap portion.

12. A flavor releasing article comprising a cigarette package containing a plurality of cigarettes, said package having an inner wrap and an overwrap, said inner wrap having a top including flaps and a pack closure disposed over said flaps, a flavor burst film disposed between said inner wrap and said overwrap, said flavor burst film comprising a flavor carrier layer having opposite surfaces and being composed of a polymeric material having a polymeric matrix, a flavorant blended with said polymeric material such that said flavorant is contained in the polymeric matrix and is capable of being released from the opposite surfaces of the flavor carrier layer, first and second barrier layers disposed on a respective one of the opposite surfaces of the flavor carrier layer for retaining the flavorant in the flavor carrier layer, said first barrier layer being affixed to a portion of said pack closure overlying said flaps and said second barrier layer being affixed to a portion of said overwrap overlying said flaps and said pack closure, a tear tape formed independently of and separate from said flavor burst film for detaching said overwrap portion overlying said flaps from the top of the inner wrap, said second barrier layer being separable from the flavor carrier layer such that when aid overwrap portion is detached from the top of the inner wrap, said second barrier layer, said overwrap portion and said tear tape separate from the flavor carrier layer and said first barrier layer and said flavor carrier layer remain attached to said pack closure portion whereby one of the surfaces of the flavor carrier layer is exposed and the flavorant is released therefrom.

13. The article of claim 12, including an adhesive layer between said first barrier layer and said flavor carrier layer for preventing separation therebetween.

14. The article of claim 12, wherein said flavor burst film is coextruded.

* * * * *